United States Patent [19]

Frey et al.

[11] Patent Number: 4,700,567
[45] Date of Patent: Oct. 20, 1987

[54] RHEOLOGY TEST SYSTEM

[75] Inventors: Emory L. Frey; David W. Looper; Eugene J. Daunis, all of Duncan, Okla.

[73] Assignee: Halliburton Company, Duncan, Okla.

[21] Appl. No.: 801,121

[22] Filed: Nov. 21, 1985

[51] Int. Cl.⁴ .................. E21B 21/06; G01N 11/04
[52] U.S. Cl. ................................... 73/151; 73/54
[58] Field of Search ............... 73/151, 155, 54, 55, 73/59, 60, 153; 166/250, 308; 364/422

[56] References Cited

U.S. PATENT DOCUMENTS 3,473,368  10/1969  Roper .............................. 73/151
4,065,959   1/1978  Richardson ........................ 73/56
4,227,404  10/1980  West .............................. 73/151

OTHER PUBLICATIONS

Halliburton Services Operator's Manual for Laminar Rheology Flow Loop.

Pictures of prior art laminar flow rheology skid, Halliburton Services, Inc., 1984.

Primary Examiner—Jerry W. Myracle
Assistant Examiner—Scott M. Oldham
Attorney, Agent, or Firm—James R. Duzan; E. Harrison Gilbert, III

[57] ABSTRACT

A rheology test system includes a self-propelled vehicle, a computer contained in the vehicle and a rheology flow loop skid mounted in an outboard storage compartment of the vehicle. The rheology flow loop skid includes an obliquely mounted helical conduit through which laminar flow is maintained. The helical loop is mounted on a base near an inboard side thereof, and instrumentation is mounted on an outboard side of the base so that the apparatus can be readily used while mounted on the vehicle. Improved connecting pipes provide a more compact construction and a more easily assemblable and disassemblable construction.

17 Claims, 10 Drawing Figures

U.S. Patent  Oct. 20, 1987  Sheet 1 of 5  4,700,567
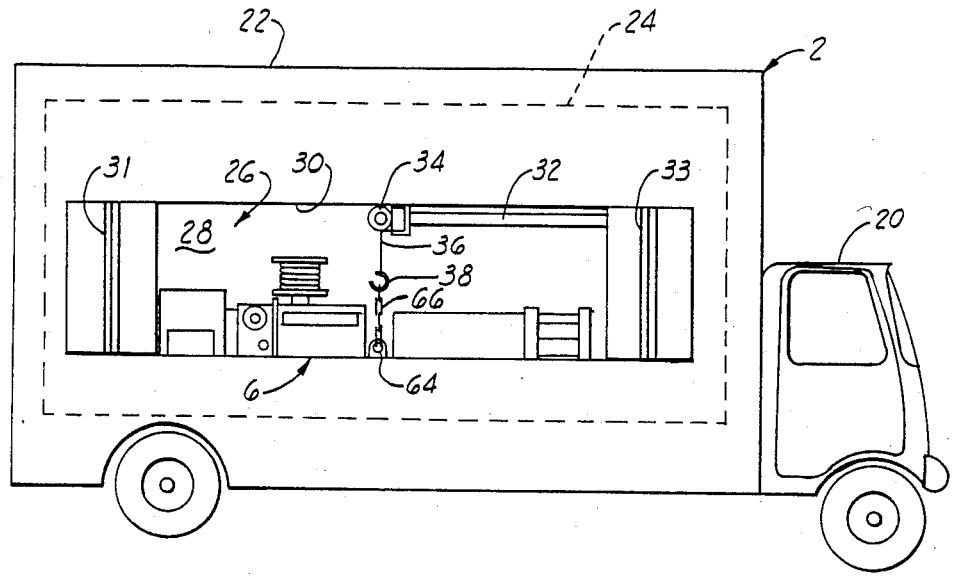
FIG. 1
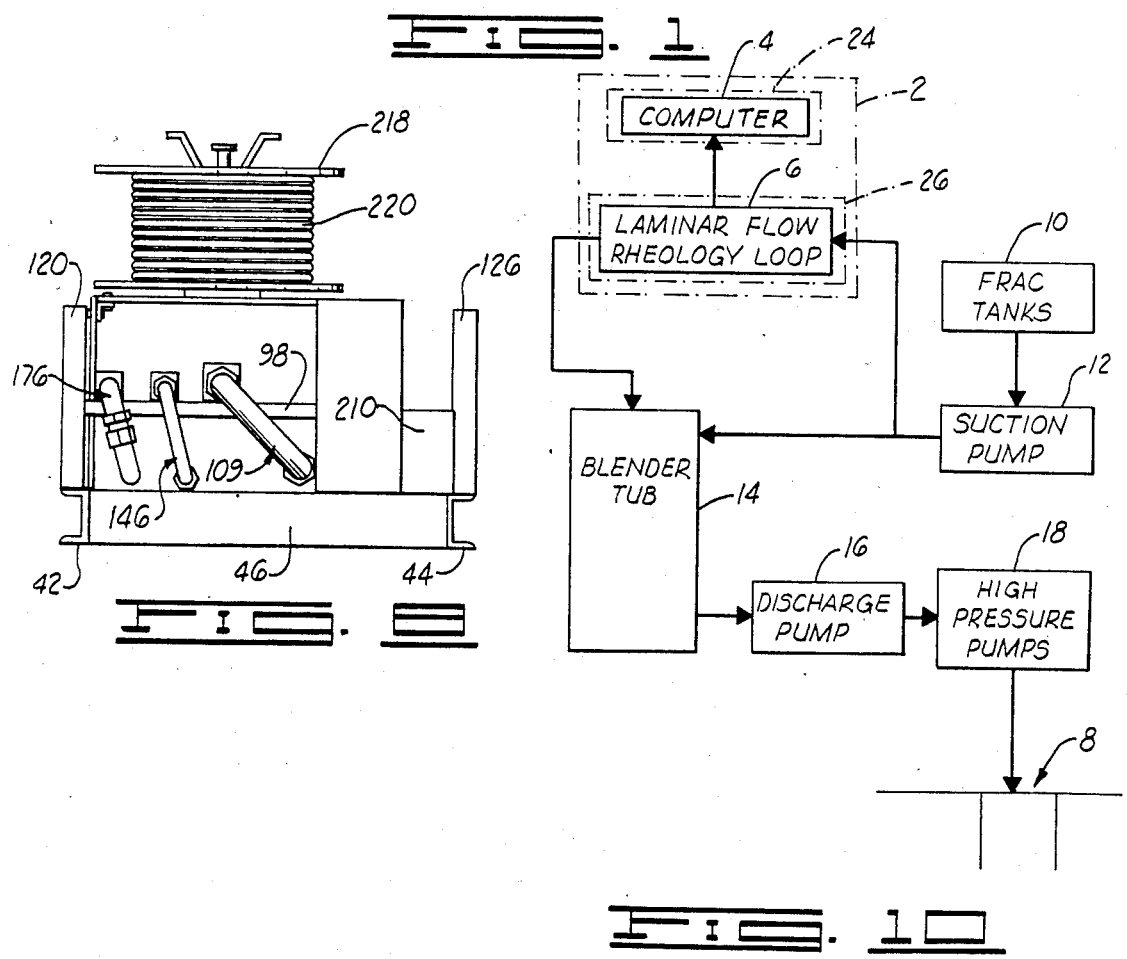
FIG. 3
FIG. 10

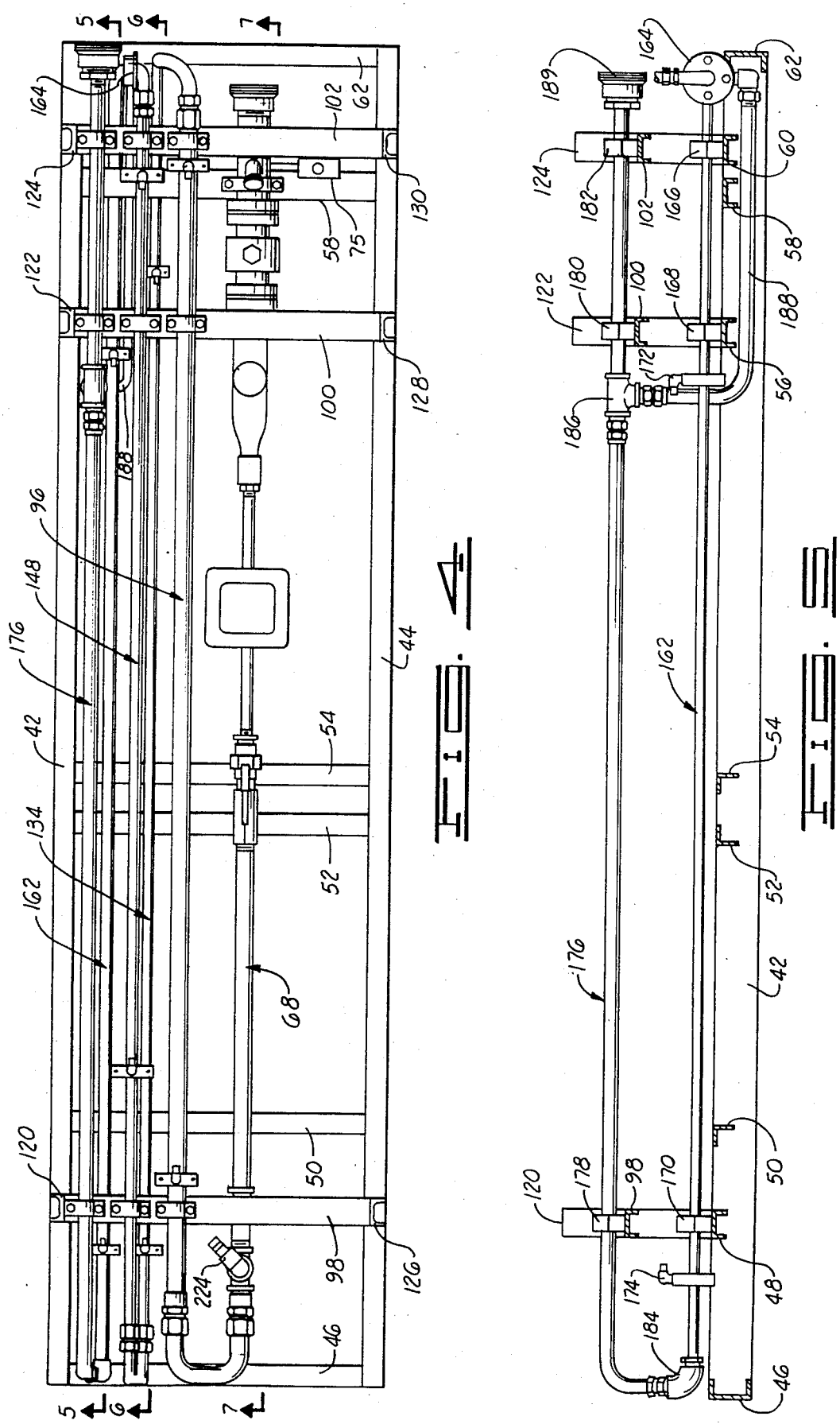

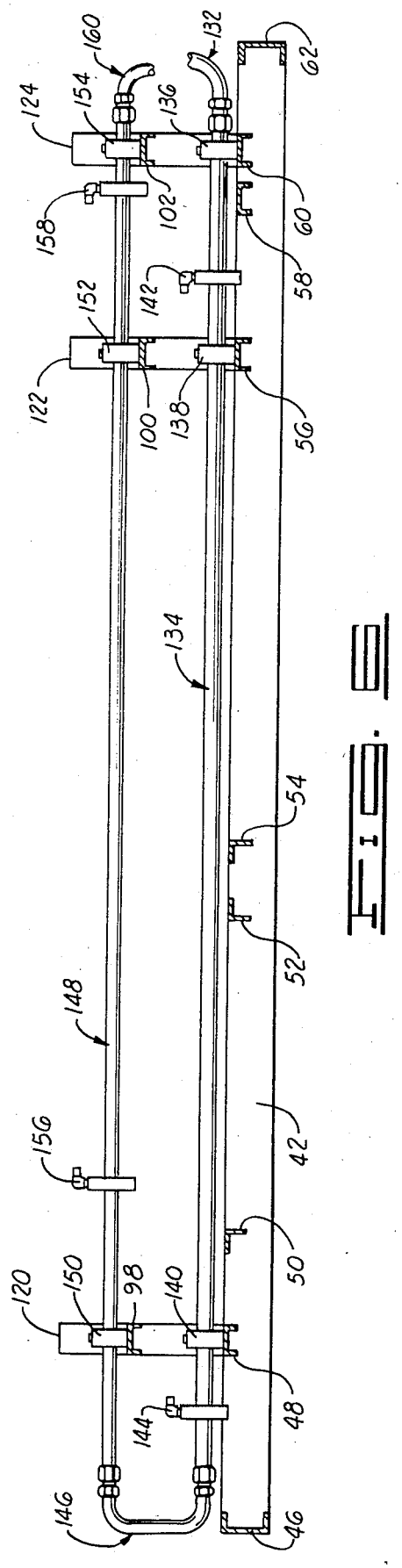
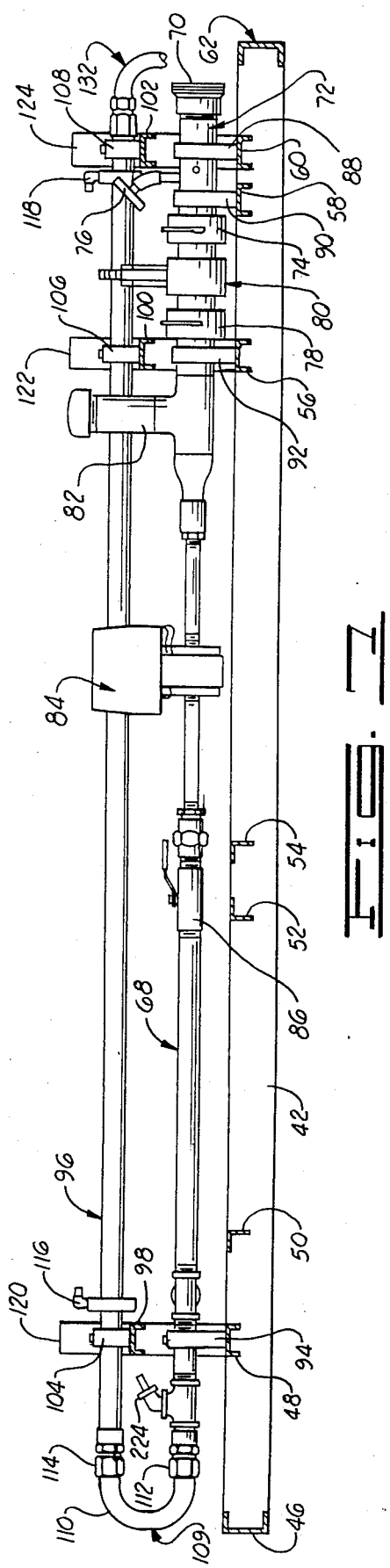

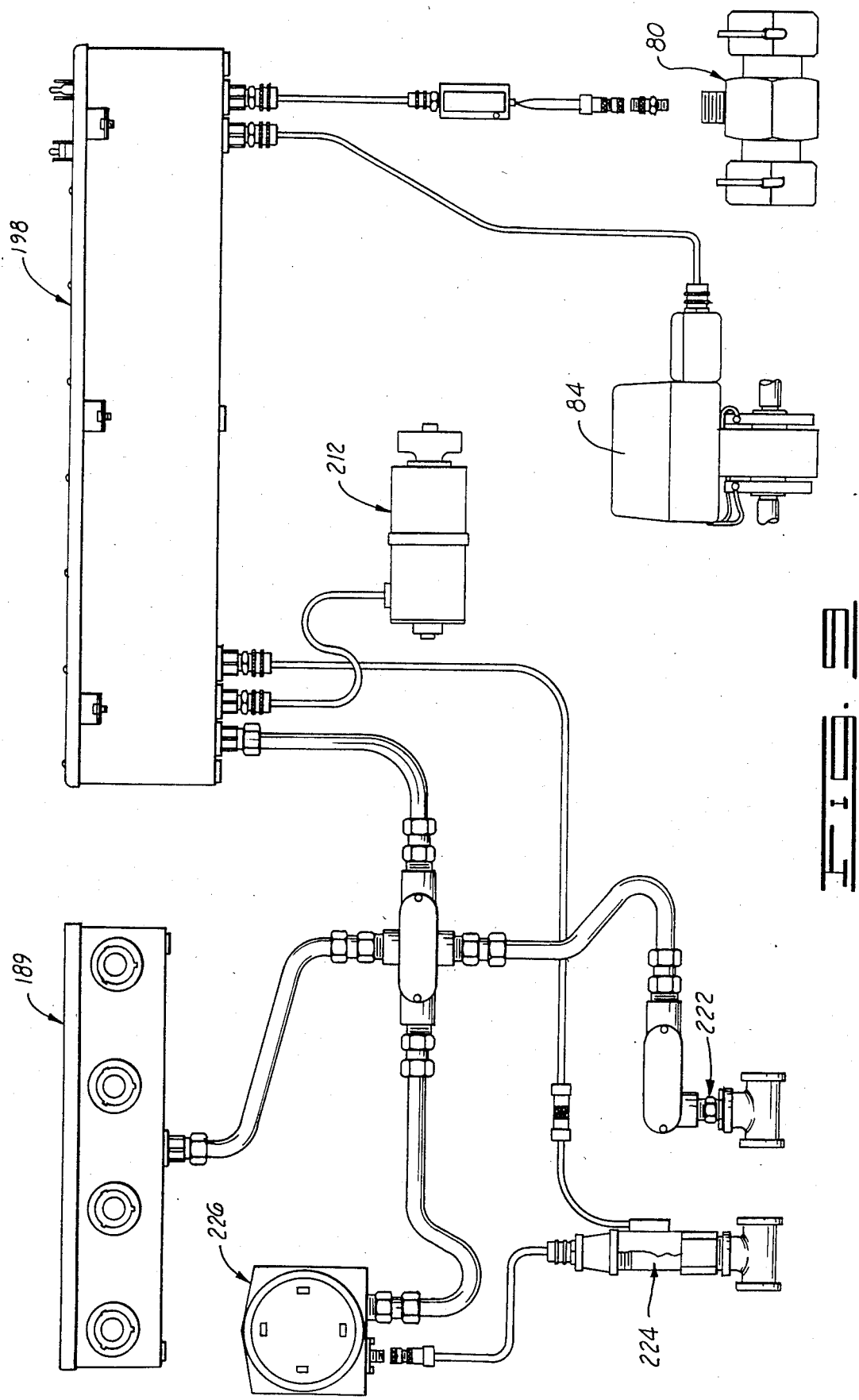

RHEOLOGY TEST SYSTEM

BACKGROUND OF THE INVENTION

This invention relates generally to rheology test apparatus and more particularly, but not by way of limitation, to a transportable rheology test system having commonly associated laminar flow rheology and computational equipment for use at a well site to predict friction pressure loss and bottom hole treating pressure, for example, during a fracturing treatment being performed on the well.

Once an oil or gas well is drilled, it is sometimes necessary to fracture a formation to improve the flowability of the hydrocarbons trapped in the formation. To perform a fracturing job, specialized fracturing fluids suitable for the specific job are blended. The fracturing fluids are developed at the well site by blending selected chemicals into a base gel, the characteristics of which gel can be controlled based upon rheological properties as determined from real-time measurements taken through the use of a laminar flow rheology loop. Such measurements can also be used for predicting friction pressure loss and bottom hole treating pressures that are likely to occur when the blended fluid is pumped downhole during the fracturing process. Such control and prediction abilities enhance the chances of obtaining a good result from the fracturing job under way, and the information obtained therefrom is helpful in designing other blends for subsequent jobs.

One technique for obtaining such control and prediction abilities is based upon the shear rate versus shear stress relationship applicable to the particular base gel being used. This relationship can be determined by monitoring differential pressures along various lengths and diameters of the flowing base gel. Measurements of such differential pressures correlate to points on a graphical representation of the particular shear rate versus shear stress relationship. For example, a least squares fit calculation can be used with the differential pressure measurements to compute a straight line having a slope representing the n' value and having a y-axis intercept representing the k' value for the shear rate versus shear stress relationship. These values are used by a computer for correlating to turbulent flow in pipes of other diameters and for providing other suitable information on a real-time basis. The mathematical relationships of this technique are known to the art.

The foregoing technique of using differential pressure measurements to develop a shear rate versus shear stress relationship that can be correlated into useful, real-time information by which the quality of a gel can be controlled and by which predictions of downhole phenomena can be made has been implemented by a portable laminar flow rheology skid developed and used by Halliburton Services prior to October, 1984. This skid is transportable by a vehicle dedicated to that function, such as a pickup truck, but it is electrically connectible to a COMPUVAN ™ testing vehicle for providing the differential pressure information to computers in the testing vehicle, which computers generate the correlations and predictions based on the differential pressure information. This skid, however, is not designed so that it can be carried by a testing vehicle such as the COMPUVAN ™ testing vehicle, thereby necessitating the use of two separate vehicles to transport both the skid and the necessary computational equipment to the well site. This prior skid is also relatively difficult to disassemble and clean.

In operation, the prior skid has been used with a blending system that includes frac tanks containing the base gel, a blender tub, a suction pump for pumping the gel from the frac tanks to the blender tub, a discharge pump for pumping the blend from the tub for subsequent high pressure pumping, by other pumps, into the well. Additives can be blended into the base gel through application into the tub or along the flow path as known to the art. The prior laminar flow rheology loop has an inlet connected to receive a portion of the clean base gel tapped from the flow between the suction pump and the tub. The rheology loop has an outlet through which the tapped portion flows into the tub.

The tapped flow circulates through at least part of the loop, which comprises four test pipe sections having different diameters (e.g., nominal inner diameters of $\frac{3}{8}$ inch, $\frac{1}{2}$ inch, $\frac{3}{4}$ inch and one inch). A respective differential pressure transducer and two respective pressure taps are used to measure the pressure drop over a specified length in each pipe section. To increase the range of gel viscosities that can be accommodated in this flow loop, only three test pipe sections are used by the computer program at any one time (in this embodiment, either the three larger pipe sections or the three smaller pipe sections). If a relatively thin fluid is being used, for example, then lower flow rates or larger pipes will keep the flow laminar. To check if the flow is laminar, the computer program makes a linear regression analysis of the differential pressure measurements from the test pipe sections and computes a correlation coefficient, R. The value of R should approach 1.0. A value of R much less than 1.0 would indicate non-laminar flow in one or more pipes or perhaps a plugged pressure tap.

To prevent the pressure taps, from which the pressure measurements are taken, from becoming plugged as well as to remove air from the lines connecting these taps to the differential pressure transducers associated with the rheology loop, a purge system is provided on the flow loop. This system includes a reservoir of purge fluid, a purge pump and eight on-off toggle valves. The purge pump supplies a suitable flow, and the toggle valves allow each tap to be purged individually. Such purging helps to insure that each pressure tap will respond as designed.

In this prior rheology loop, the flow rate of the base gel being circulated through the loop must also be controlled and measured. The flow rate is controlled by a 1-inch ball valve, and the flow rate is measured in one of two different ways, depending on the type of gel being circulated. If an agueous (conductive) gel is circulated through the loop, a magnetic flow meter measures the flow rate. If a non-aqueous (non-conductive) gel is circulated, a standard turbine flow meter measures the flow rate.

The prior skid also includes a pH probe and temperature probe placed in the flow stream to monitor these characteristics of the base gel.

The prior skid also includes a bypass valve so that the $\frac{3}{8}$-inch test pipe section can be removed from the flow stream. This is used not only to select between which set of three test pipe sections is to be used, but also to bypass the smallest pipe should the outlet pressure of the blender tub become marginal whereby such bypassing decreases the back pressure that the laminar flow loop creates in the portion of the flow taken from the blender tub.

Although this prior skid functions satisfactorily, there is the need for an improved rheology test system constructed so that a rheology flow loop skid thereof can be conveniently and readily transported on a complementally constructed vehicle also capable of carrying the computation equipment needed to perform the necessary calculations. It is also desirable for such an improved loop to be constructed so that at least parts of it can be more easily disassembled and the loop more easily cleaned than in the prior skid.

SUMMARY OF THE INVENTION

The present invention overcomes the above-noted and other shortcomings of the prior art by providing a novel and improved rheology test system. This system includes a skid-mounted laminar flow rheology loop which is more compact and lighter in weight than the aforementioned prior rheology skid so that the present invention can be carried by a complementally constructed test vehicle also carrying computational equipment forming another part of the overall system. The improved rheology skid, itself, is constructed, at least in part, of parts that can be more readily disassembled and cleaned than can be done in the prior skid.

Broadly, the present invention provides a transportable rheology test system that comprises a self-propelled vehicle including a housing having inboard storage means for receiving electronic computational equipment and also having a storage compartment and that also comprises rheology flow loop means, disposed in the storage compartment, for measuring a differential pressure across a portion of a substance flowing through the rheology flow loop means for use by the electronic computational equipment. The vehicle also includes hoist means for moving the rheology flow loop means into and out of the storage compartment.

More particularly defined, the present invention provides a transportable rheology test system for generating, at the location of a well, predictions of friction pressure loss and bottom hole treating pressure during a fracturing treatment being performed on the well, which system comprises: a self-propelled vehicle for moving the system to a well site; computer means, mounted in the vehicle, for calculating, in response to differential pressure values, n' and k' parameters of a shear rate versus shear stress relationship of a flowing substance, from which parameters the predictions are generated; and rheology flow loop means, removably disposed on the vehicle, for detecting a plurality of differential pressure values along a plurality of lengths of a substance flowing therethrough and for providing to the computer means signals representing the plurality of differential pressure values.

The rheology flow loop means more particularly includes a base and a helical pipe assembly mounted on the base, the assembly including a plurality of lower pipe sections and a plurality of upper pipe sections and a plurality of connecting pipe sections disposed so that each connecting pipe section connects a respective one of the lower pipe sections with a respective one of the upper pipe sections. In the preferred embodiment each connecting pipe section extends obliquely relative to the base so that the upper and lower pipe sections are spaced a vertical distance which is less than the length of the connecting pipe sections, thereby providing a more compact construction. Additionally, each of the connecting pipe sections of the preferred embodiment includes coupling means for releasably coupling the respective connecting pipe section with its respective upper and lower pipe sections, thereby facilitating disassembly and cleaning of the flow loop. In the preferred embodiment the base has a longitudinal side, and the rheology apparatus further comprises instrumentation means for transferring information from the apparatus, which instrumentation means is mounted on the base along the longitudinal side so that it is readily usable when the apparatus is mounted on the preferred embodiment of the self-propelled vehicle.

Therefore, from the foregoing, it is a general object of the present invention to provide a novel and improved rheology test system. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 1 is a schematic illustration showing the preferred embodiment of the system of the present invention including a self-propelled vehicle and a laminar flow rheology skid.

FIG. 4 is a plan view of the skid showing only the base and the primary flow loop.

FIG. 5 is a sectional side elevational view taken along line 5—5 shown in FIG. 4.

FIG. 6 is a sectional side elevational view taken along line 6—6 of FIG. 4.

FIG. 7 is a sectional side elevational view taken along line 7—7 shown in FIG. 4.

FIG. 8 is an end elevational view of the rheology skid.

FIG. 9 is a schematic circuit diagram of the instrumentation and electronics interconnections of the skid.

FIG. 10 is a block diagram showing the present invention in a specific environment at an oil or gas well site.

DETAILED DESCRIPTION OF THE PREFERRED EMBODIMENT

Figures 2, 3:
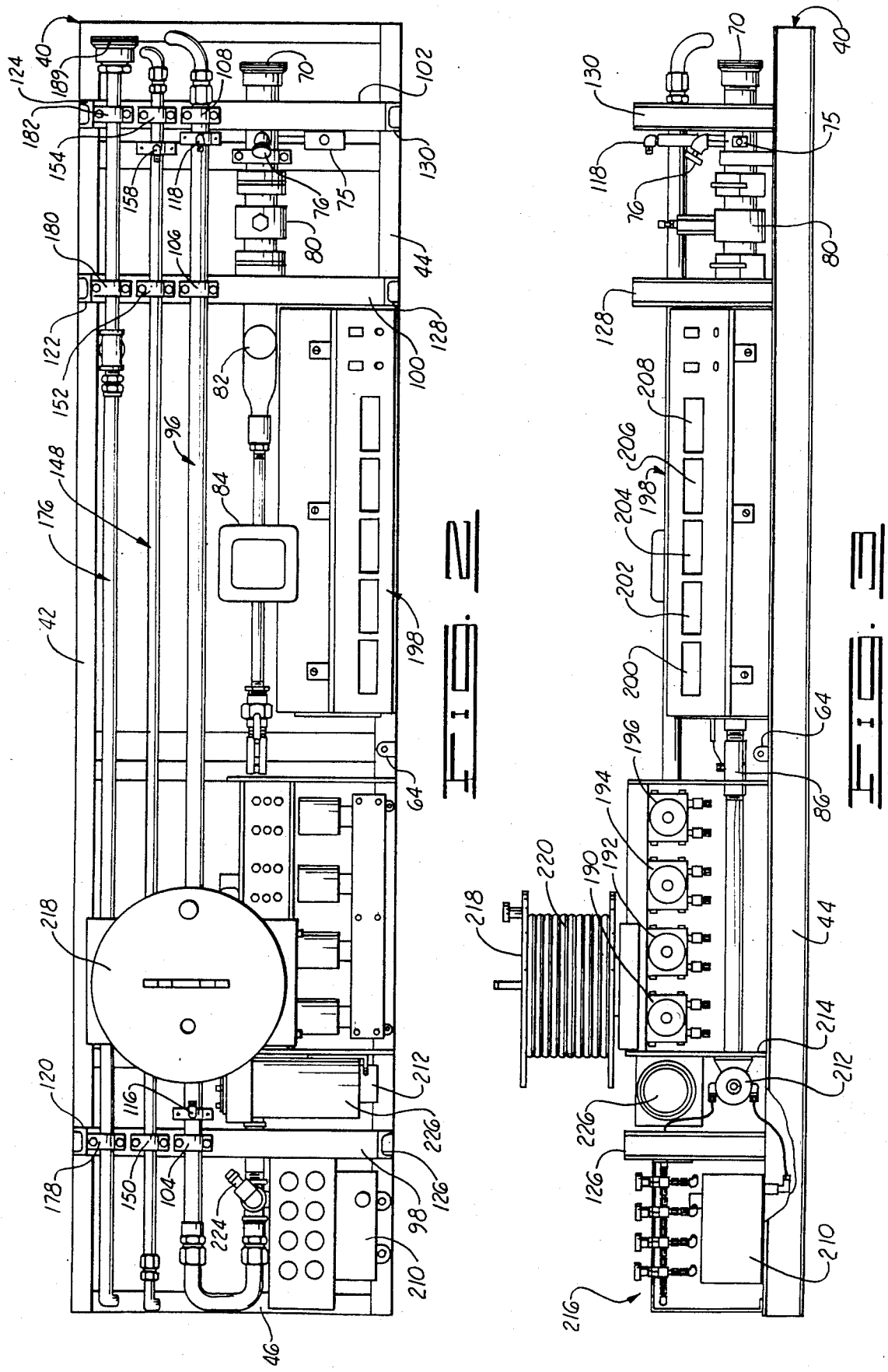
FIG. 2 is a plan view of the rheology skid of the preferred embodiment wherein the lower laminar flow pipe sections are omitted for clarity.
FIG. 3 is a side elevational view of the rheology skid shown in FIG. 2.

FIGS. 1 and 10 generally show that the preferred embodiment of the present invention includes a self-propelled vehicle 2 having a computer 4 and a rheology flow loop means 6 suitably mounted therein. This combination is shown in FIG. 10 in use at a well site 8 where one or more tanks 10 of fracturing fluid or base gel, a suction pump 12, a blender tub 14, a discharge pump 16 and high pressure pumps 18 are also located. The elements 10, 12, 14, 16 and 18 are of suitable types as known to the art for producing a suitable fracturing fluid to be pumped into the well at the site 8 for performing a fracturing job as known to the art. Additional equipment, such as means for introducing additional chemicals into the blender tub and general flow path, can also be incorporated in the fracturing fluid system as known to the art. In this specific environment the present invention provides a transportable rheology test system for generating, at the well site 8, predictions of friction pressure loss and bottom hole treating pressure during the fracturing treatment being performed on the well; however, the present invention can be put to other suitable uses wherein differential pressure measurements for different cross-sectional flows of fluid are needed.

The self-propelled vehicle 2 of the preferred embodiment is specifically the COMPUVAN ™ test vehicle of Halliburton Services. Such a vehicle 2 includes a driver/operator cab 20 and a housing 22. The housing 22 has an inboard storage compartment 24 in which various types of equipment, including electronic computational equipment, are stored as known to the art. For example, the computer 4 is suitably mounted in the inboard storage compartment 24. The housing 22 also includes an outboard storage compartment for receiving the rheology flow loop means 6. This compartment is shown in FIG. 1 and generally identified by the reference numeral 26. The compartment 26 is defined by a cavity having a closed interior as defined in part by a back wall 28, which extends vertically from a shelf on which the means 6 is placed. The cavity opens to the outside of the vehicle 2 through an outboard opening 30, which is closed by means of suitable folding doors 31, 33.

The vehicle 2 also includes hoist means, disposed in the storage compartment 26, for lifting and lowering the flow loop means 6 into and out of the storage compartment 26. The hoist means includes a support frame having a horizontally pivotable arm or beam 32 to which a sheave 34 is journaled. A cable 36 depends over the sheave 34 to a hook 38. By connecting the flow loop means 6 to the hook 38 and suitably actuating a drive mechanism (not shown) to take up the cable 36, the flow loop means 6 can be raised off the lower shelf of the storage compartment 26, whereupon the arm 32 can be pivoted outwardly and the cable 36 subsequently played out to lower the flow loop means 6 to the ground or other suitable platform outside of the housing 22 of the vehicle 2. In the preferred embodiment the hoist means is mounted within the outboard storage compartment 26 as shown in FIG. 1.

The computer 4 depicted in FIG. 10 and retained in the inboard storage compartment 24 of the vehicle 2 is any suitable computational device programmed to perform the necessary algorithms for receiving the differential pressure information from the flow loop means 6 and for converting that information into the desired output. In the preferred embodiment this computer means is used for calculating in response to the differential pressure values the n' and k' parameters of a shear rate versus shear stress relationship of the substance, such as the base gel in the exemplary environment, flowing through the flow loop. The computer means is further programmed to utilize these parameters for generating the friction pressure loss and bottom hole treating pressure predictions. Such programming is of a type as known or readily known to those skilled in the art, such as of the type used with the previously described prior art rheology flow loop described hereinabove. For example, a least squares fit calculation is used for computing the n' and k' values from the differential pressure measurements obtained with the flow loop means 6.

With reference to FIGS. 2–9, the preferred embodiment of the rheology flow loop means 6 of the present invention will be described. Generally, the means 6 is constructed for detecting differential pressures across portions of a substance flowing through the flow loop means 6. In this regard, the means 6 is similar to the rheology flow loop of the prior art; however, the present invention is constructed more compactly and for easier assembly and disassembly than is the prior art rheology flow loop. In this improved construction of the present invention, the flow loop means 6 broadly includes a base 40 and a helical pipe assembly or tubing obliquely connected to the base 40. Other elements of the preferred embodiment will be subsequently described hereinbelow.

FIGS. 2–7 show that the base 40 includes two parallel longitudinal side beams 42, 44 separated by perpendicularly or laterally extending cross members 46, 48, 50, 52, 54, 56, 58, 60, 62, which elements are of a suitable material, such as aluminum whereby a relatively lightweight, but structurally rugged frame is provided. These elements define a substantially rectangular frame which is horizontally disposed when it is placed in the storage compartment 26. When it is so placed, the longitudinal side beam 42 constitutes an inboard side disposed adjacent the back wall 28, and the longitudinal side beam 44 constitutes an outboard side disposed adjacent the opening 30 of the storage compartment 26. This positioning is important to the proper utilization of the present invention as will become more readily apparent hereinbelow when the placement of the instrumentation elements is described.

As shown in FIG. 1, attached to the base 40 is an eyelet member 64 to which a chain or cable 66 is connected at one end thereof. The other end of the member 66 is connected to the hook 38. These elements define means for connecting the base 40 and the hoist means whereby the hoist means can raise and lower the base 40 to removably dispose the flow loop means 6 relative to the storage compartment 26 and the vehicle 2.

As shown in the plan views of FIGS. 2 and 4, the base 40 has the helical pipe assembly mounted thereon nearer to the inboard side defined by the beam 42 than to the outboard side defined by the beam 44. One unique feature of the helical pipe assembly of the present invention is its helical or corkscrew construction whereby the pipe assembly is defined by sections of pipe at alternating flow heights. By this construction, the fluid under test alternately flows from one level or height to another level or height. Each convolution of the complete helical construction is shown in FIGS. 5, 6, and 7 with the inlet convolution shown in FIG. 7.

The inlet convolution shown in FIG. 7 includes a horizontally extending linear inlet pipe section 68 longitudinally mounted on the base 40 centrally between the two longitudinal sides 42, 44. This pipe section 68 is mounted at the lower of the two heights at which the pipe sections are disposed in the preferred embodiment. The inlet pipe section 68 includes a threaded inlet manifold coupling 70. The coupling 70 is connected through a tubing section 72 to a Victaulic coupling 74. A pressure gauge 76 is connected into the tubing portion 72, from which there extends a ball valve 75 and a conduit through which a sample of fluid can be extracted for further analysis such as by a field chemist. Connected between the coupling 74 and another Victaulic coupling 78 is a turbine flow meter 80, which measures the flow rates of non-conductive fluids having less than 33% conductive fluid (a mass flow meter can be optionally used). A stand pipe 82 for controlling flow fluctuations through the flow loop means 6 is connected downstream of the coupling 78. A magnetic flow meter assembly 84, which measures conductive water-based fluids having greater than 33% conductive fluid, is connected between the stand pipe 82 and a ball valve 86 by which the flow rate of the gel flowing through the flow loop means 6 is controlled. The inlet pipe section 68 and the aforementioned elements disposed therein are supported at the lower height relative to the base 40 by suitable clamp members 88, 90, 92, 94.

Connected to the outlet end of the inlet pipe section 68 is a first linear laminar flow pipe section 96 spaced vertically and horizontally from the inlet pipe section 68. The pipe section 96 extends horizontally and is disposed at a second height relative to the base 40. The pipe section 96 is supported at this height by cross support members 98, 100, 102, and suitable clamp members 104, 106, 108. The support members 98, 100, 102 are vertically supported by vertical support braces 120, 122, 124, 126, 128, 130.

The connection between the outlet end of the pipe section 68 and the inlet end of the pipe section 96 is made by means of a suitable connecting pipe section 109 provided in the preferred embodiment by a stainless steel tubing 110 having releasable compression fittings 112, 114 connected therewith. The section 109 has a predetermined length, but it is disposed obliquely (approximately 15° from vertical in the preferred embodiment) relative to the base 40 (see FIG. 8) so that the upper and lower pipe sections 96, 68 are spaced from each other by a vertical distance which is less than the predetermined length of the connecting pipe section 109. This gives the unique "laid-over" or oblique construction of the helical tubing by which a height-saving is achieved over a construction wherein upper and lower pipe sections are vertically aligned. Use of the compression fittings 112, 114 allows the connecting pipe section 109 to be rapidly connected to or disconnected from the pipe sections 68, 96 for enhancing the ability to quickly assemble or disassemble, and also to quickly clean, the pipe sections 68, 96. Another feature of the connecting pipe section 109 is that it can be made shorter than a welded union connection, which is the type of connection in the prior art rheology flow loop. The stainless steel tubing 110 and compression fittings 112, 114 also provide better interfacing between flow sections whereby smoother flow is maintained between pipe sections.

Connected to the flow pipe section 96 is a pair of spaced pressure taps 116, 118 by which the pressures at the two ends of the differential pressure section, defined by the spacing of the taps 116, 118, are communicated to a respective differential pressure transducer subsequently described.

Extending from the outlet end of the first laminar flow pipe section 96 is another connecting pipe section 132 constructed similarly to the section 109, except that the section 132 is sized to make a smooth transition between the nominal 1-inch inner diameter of the laminar flow section 96 and the nominal ¾-inch inner diameter of a linear laminar flow pipe section 134. The linear laminar flow pipe section 134 forms another part of the lower pipe sections of the flow loop of the preferred embodiment, which lower pipe sections also include the inlet pipe section 68. Thus, the pipe section 134 is disposed at substantially the same height as the pipe section 68 relative to the base 40. This height is maintained by suitable clamping members 136, 138, 140 supported by the cross members 60, 56, 48, respectively. Connected into the flow pipe section 134 is another pair of pressure taps 142, 144.

Disposed in the upper pipe sections and connected by a connecting pipe section 146 is a linear laminar flow pipe section 148 connected to the base 40 by means of clamps 150, 152, 154, and spaced vertically and horizontally from the laminar flow pipe section 134. The nominal inner diameter of the flow pipe section 148 is ½ inch; therefore, the connecting pipe section 146 provides a suitable transition from the ¾-inch nominal inner diameter of the lower flow pipe section 134. Connected into the flow pipe section 148 are pressure taps 156, 158.

The outlet end of the pipe section 148 is connected through a connecting pipe section 160 to a linear laminar flow pipe section 162 having a ⅜-inch nominal inner diameter, the transition to which is made through the connecting pipe section 160. Forming part of the interface between the pipe section 148 and the pipe section 162 is a bypass valve 164 by which the flow pipe section 162 can be bypassed if only the three larger diameter flow pipe sections 96, 134, 148 are used to detect differential pressures of the substance flowing through the flow loop of the present invention. The flow pipe section 162 is mounted at the lower height similarly to the flow pipe sections 68, 134. This mounting is by means of suitable clamps 166, 168, 170 as shown in FIG. 5. Pressure taps 172, 174 are connected into the pipe section 162.

A linear outlet pipe section 176 is retained at the upper height by clamps 178, 180, 182 and is connected to the lower pipe section 162 through an elbow coupling 184. A tee connector 186 forms part of the pipe section 176, which tee connector 186 has a stem connected through a bypass pipe 188 to the bypass valve 164 as shown in FIG. 5. The outlet pipe section 176 terminates in a suitable coupling member 189. A hose or other conduit is connected to the coupling 189 for transferring the fluid from the flow loop means 6 to the blender tub 14 as illustrated in FIG. 10. As with the other upper pipe sections, the outlet pipe section 176 is spaced vertically and horizontally from its immediately preceding lower pipe section, which is pipe section 162 in the illustrated embodiment.

From the aforementioned assemblage of pipe sections, a single continuous rheology test flow path or conduit is defined through the rheology flow loop means 6. Yet, contained within this single continuous flow path are linear sections having different cross-sectional areas and along which different differential pressures can be measured in response to the pressures communicated through the various pairs of pressure taps. These pressures are communicated to instrumentation means for transferring information from the flow loop means 6 to an operator or to the computer 4. The instrumentation means of the preferred embodiment includes four differential pressure transducers 190, 192, 194, 196 linearly aligned and connected to the base 40 along the outboard longitudinal side 44. Each of the transducers 190, 192, 194, 196 is connected to a respective pair of the pressure taps previously described. The electrical output from these pressure transducers, which are energized by a suitable source such as a 12 VDC battery found in the vehicle 2, are provided both to the computer 4 and to a display means 198 for displaying the differential pressures. The display means 198, forming another part of the instrumentation means, includes five digital readouts 200, 202, 204, 206, 208. Four of these readouts display the four differential pressures from the four laminar flow test sections 96, 134, 148, 162, and the fifth one visually displays the flow rate detected by whichever one of the flow meters 80, 84 is used. The readouts 200, 202, 204, 206, 208 are substantially linearly aligned with each other and with the transducers 190, 192, 194, 196. The readouts are mounted along the outboard beam 44 so that the informational signals provided through the readouts can be directly and readily observed by the operator even when the flow loop means 6 is mounted in the storage compartment 26. Such positioning of these elements places the instrumentation means in parallel relationship with the helical tubing section, but spaced therefrom along the outboard longitudinal side of the base 40.

The plurality of pressure taps are connected to the respective transducers by plastic tubing lines of types as known to the art, but which are not shown in the drawings for purposes of simplicity. It is through the pressure taps and the tubing lines that the various pressures are communicated to the respective transducers.

The flow loop means 6 also includes purge means for purging each of the pressure taps to prevent them from becoming plugged or otherwise blocked. The purge means includes a reservoir 210 mounted on the base 40 along the outboard side beam 44 in alignment with the instrumentation means including the previously described pressure transducers and digital readouts (see FIGS. 2 and 3). The purge means also includes a pump 212 attached to a support member 214. The pump 212 pumps a suitable purge fluid from the reservoir 210 to one or more selected ones of the pressure taps, which selection is made through suitable valves 216 for controlling the flow of the purge fluid to the pressure taps.

FIGS. 1, 2, 3 and 8 also show a reel 218 upon which an electrical cable 220 is wound. These two elements are not necessarily integral parts of the flow loop as initially constructed in its preferred embodiment. Rather, the reel 218 and the cable 220 can be mounted in the field if so needed or desired; however, at least a cable of a suitable type is needed, in general, because a cable, such as the cable 220, is used to electrically connect the flow loop means 6 to the electronic equipment in the vehicle 2. A reel of cable is illustrated so that there is sufficient cable to maintain the electrical connection even when the flow loop means 6 is removed from the storage compartment 26.

FIG. 9 shows the cabling interconnections and the use of conduits through which electrical wires are run for interconnecting various electronic elements of the preferred embodiment of the present invention. These elements shown in FIG. 9 correspond to those previously described as indicated by the like reference numerals. Two elements not previously described but included in the preferred embodiment are a temperature probe 222 and a pH sensing assembly including a pH probe 224 and a pH transmitter 226, which elements are connected into the flow loop in a manner as known to the art.

The operation of the present invention is similar to the operation of the prior skid described hereinabove in that a fluid, such as the base gel to be used in developing a fracturing fluid, flows through the different diameter flow pipe sections from which the various differential pressures can be monitored. By using the bypass valve 164, either the three larger diameter flow pipe sections or the three smaller diameter flow pipe sections can be used during any one test. Which one of these is used is coordinated with the program being run in the computer 4 as known to the art.

As in the prior flow loop, the base gel is supplied to the present invention from the clean side or suction side of the blender tub 14. The fluid flows through the flow meters 80, 84 and the control valve 86 which controls the flow rate. The fluid passes through the 1-inch laminar flow pipe section 96, and the pressure drop is measured over a specified distance defined by the spacing of the pressure taps 116, 118 (this measurement is made if the larger pipe diameter option has been selected). The fluid continues through the $\frac{3}{4}$-inch pipe section 134; the pressure drop through this section is measured across the specified distance defined between the pressure taps 142, 144. The fluid next flows through the $\frac{1}{2}$-inch pipe section 148 along which the differential pressure is measured across the length defined by the spacing of the pressure taps 156, 158. If selected through the bypass valve 164, the fluid then flows through the $\frac{3}{8}$-inch pipe section 162 so that the differential pressure across the length defined between the pressure taps 172, 174 is measured. The fluid then flows out through the coupling 189 into the blender tub 14. If the valve 164 has been operated to bypass the $\frac{3}{8}$-inch pipe section 162, the fluid exits through the bypass pipe 188 and the outlet coupling 189.

With the differential pressure measurements obtained from the aforementioned flow, which flow is controlled so that it is laminar rather than turbulent, the graph of the fluid shear rate versus the fluid shear stress relationship for the specific base gel can be computed by using the least squares fit calculation for a straight line through the differential pressure points. From this computation, the n' and k' values are obtained for further use by the computer for correlation to turbulent flow in pipes of other diameters and other information such as quality control of the base gel or predictions of friction pressure loss and bottom hole treating pressure.

By the foregoing construction of the present invention, a shorter, lighter and, generally, more compact rheology flow loop skid is provided, which flow loop can be more easily assembled and diassembled and thus more easily cleaned than can be done in the prior rheology flow loop described hereinabove. With this construction, the system of the present invention, including the combination of a single self-propelled vehicle carrying both computational equipment and the rheology flow loop skid, is provided. Thus, the present invention is well adapted to carry out the objects and attain the ends and advantages mentioned above as well as those inherent therein. While a preferred embodiment of the invention has been described for the purpose of this disclosure, numerous changes in the construction and arrangement of parts can be made by those skilled in the art, which changes are encompassed within the spirit of this invention as defined by the appended claims.

What is claimed is:

1. A transportable rheology test system, comprising:
   a self-propelled vehicle including a housing having in board storage means defined therein for receiving electronic computational equipment and said housing also having a storage compartment defined therein; and
   rheology flow loop means, disposed in said storage compartment, for measuring a differential pressure across a portion of a substance flowing through said rheology flow loop means for use by the electronic computational equipment, said rheology flow loop means including a horizontal base having secured thereto a flow pipe assembly defining a flow path for said substance which substantially changes horizontal direction only when reaching a substantially different vertical height with respect to said base.

2. A system as defined in claim 1, wherein said pipe assembly includes:
- a horizontal inlet pipe section disposed at a first height relative to said base;
- a horizontal laminar flow pipe section disposed at a second height relative to said base; and
- a connecting pipe section extending between said inlet pipe section and said laminar flow pipe section, said connecting pipe section having a predetermined length and said connecting pipe section being disposed obliquely relative to said base so that said laminar flow pipe section and said inlet pipe section are spaced a vertical distance less than said predetermined length of said connecting pipe section.

3. A system as defined in claim 1, wherein said storage compartment includes a cavity defined in an outboard portion of said housing so that said cavity opens to the outside of said vehicle through an outboard opening of said cavity, and wherein said rheology flow loop means includes:
- a base having an inboard side and an outboard side;
- a flow pipe assembly mounted on said base nearer to said inboard side; and
- instrumentation means for transferring informational signals from said rheology flow loop means, said instrumentation means mounted on said outboard side of said base and connected to said flow pipe assembly so that said informational signals are directly accessible through said outboard opening of said cavity when said rheology flow loop means is disposed therein.

4. A system as defined in claim 3, wherein said flow pipe assembly includes a helical tubing obliquely connected to said base.

5. A system as defined in claim 3, wherein said vehicle further includes hoist means, disposed in said cavity, for raising and lowering said rheology flow loop means relative to said cavity.

6. A system as defined in claim 1, wherein said vehicle further includes hoist means for moving said rheology flow loop means into and out of said storage compartment.

7. A transportable rheology test system for generating, at the location of a well, predictions of friction pressure loss and bottom hole treating pressure during a fracturing treatment being performed on the well, comprising:
- a self-propelled vehicle for moving said system to a well site;
- computer means, mounted in said vehicle, for calculating, in response to differential pressure values, n' and k' parameters of a shear rate versus shear stress relationship of a flowing substance, from which said parameters the predictions are generated; and
- rheology flow loop means, removably disposed on said vehicle, for detecting a plurality of differential pressure values along a plurality of lengths of a substance flowing therethrough and for providing to said computer means signals representing the plurality of differential pressure values, said rheology flow loop means including a base and a helical pipe assembly connected to said base.

8. A system as defined in claim 7, wherein said vehicle includes:
- a housing having a storage compartment defined therein for receiving said rheology flow loop means; and
- hoist means, disposed in said storage compartment, for lifting and lowering said rheology flow loop means into and out of said storage compartment.

9. A laminar flow rheology apparatus, comprising:
- a base; and
- a helical pipe assembly mounted on said base, said assembly including a plurality of lower pipe sections and a plurality of upper pipe sections and a plurality of connecting pipe sections disposed so that each connecting pipe section connects a respective one of said lower pipe sections with a respective one of said upper pipe sections.

10. A system as defined in claim 9, wherein each of said connecting pipe sections extends obliquely relative to said base so that said upper and lower pipe sections are spaced a vertical distance less than the length of said connecting pipe sections.

11. A system as defined in claim 10, wherein each of said connecting pipe sections includes coupling means for releasably coupling the respective connecting pipe section with its respective upper and lower pipe sections.

12. A system as defined in claim 11, wherein:
said base has a longitudinal side; and
said apparatus further comprises instrumentation means for transferring information from said apparatus, said instrumentation means mounted on said base along said longitudinal side.

13. A system as defined in claim 12, wherein:
said apparatus further comprises a plurality of pairs of pressure tap means, disposed in said pipe assembly, for communicating pressure of a substance flowing through said pipe assembly; and
said instrumentation means includes:
- a plurality of differential pressure transducers linearly aligned and connected to said base along said longitudinal side, each of said transducers connected to a respective pair of said pressure tap means; and
a plurality of display means for displaying differential pressures detected by said transducers, said display means connected to said base along said longitudinal side in substantial alignment with said transducers.

14. A system as defined in claim 9, wherein:
said base includes two longitudinal sides;
said pipe assembly includes:
- a linear inlet pipe section longitudinally mounted on said base as one of said lower pipe sections centrally between said two longitudinal sides of said base;
- a first linear laminar flow pipe section connected to said base as one of said upper pipe sections and spaced vertically and horizontally from said inlet pipe section;
- a second linear laminar flow pipe section connected to said base as another of said lower pipe sections and spaced vertically from said first linear laminar flow pipe section;
- a third linear laminar flow pipe section connected to said base as another of said upper pipe sections and spaced vertically and horizontally from said second linear laminar flow pipe section;
- a fourth linear laminar flow pipe section connected to said base as still another of said lower pipe sections and spaced vertically from said third linear laminar flow pipe section;
- a linear outlet pipe section connected to said base near a first one of said two longitudinal sides of said base as still another of said upper pipe sections and spaced vertically and horizontally from said fourth linear laminar flow pipe section; and wherein said connecting pipe sections connect said inlet pipe section, said first linear laminar flow pipe section, said second linear laminar flow pipe section, said third linear laminar flow pipe section, said fourth linear laminar flow pipe section and said outlet pipe section so that a single continuous flow path is provided therethrough; and said apparatus further comprises instrumentation means for transferring information from said apparatus, said instrumentation means mounted on said base adjacent a second one of said two longitudinal sides in parallel relationship with said pipe assembly.

15. A system as defined in claim 14, further comprising:
a plurality of pairs of pressure taps, each pair of pressure taps connected with a respective one of said first, second, third and fourth linear laminar flow pipe sections; and purge means for purging each of said pressure taps, said purge means including:
  a reservoir of purge fluid mounted on said base along said second one of said two longitudinal sides and spaced from said instrumentation means;
  pump means, mounted on said base along said second one of said two longitudinal sides adjacent said instrumentation means, for pumping the purge fluid from said reservoir; and
  valve means, mounted above said reservoir, for controlling the flow of the purge fluid to said pressure taps.

16. A system as defined in claim 9, wherein each of said connecting pipe sections includes compressive coupling means for releasably coupling with the respective lower and upper pipe sections.

17. A system as defined in claim 9, wherein:
said base has a longitudinal side; and
said apparatus further comprises instrumentation means for transferring information from said apparatus, said instrumentation means mounted on said base along said longitudinal side.

* * * * *